(12) United States Patent
Ryan et al.

(10) Patent No.: US 7,937,133 B2
(45) Date of Patent: May 3, 2011

(54) METHOD FOR DETERMINING SIZE, PATHOLOGY, AND VOLUME OF EMBOLIC MATERIAL

(75) Inventors: Ari Ryan, Mountain View, CA (US); Robert C. Glines, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 708 days.

(21) Appl. No.: 11/762,567

(22) Filed: Jun. 13, 2007

(65) Prior Publication Data
US 2007/0299337 A1 Dec. 27, 2007

Related U.S. Application Data

(60) Provisional application No. 60/805,827, filed on Jun. 26, 2006.

(51) Int. Cl.
*A61B 5/05* (2006.01)

(52) U.S. Cl. ........ 600/425; 600/423; 600/433; 600/434; 600/435; 600/466; 600/467; 382/128

(58) Field of Classification Search .................. 600/421, 600/425, 462, 469, 466, 467
See application file for complete search history.

(56) References Cited

U.S. PATENT DOCUMENTS

| | | | |
|---|---|---|---|
| 5,053,008 A | 10/1991 | Bajaj | |
| 5,348,015 A | 9/1994 | Moehring et al. | |
| 5,941,869 A | 8/1999 | Patterson et al. | |
| 6,319,242 B1 | 11/2001 | Patterson et al. | |
| 6,463,317 B1 | 10/2002 | Kucharczyk et al. | |
| 6,485,413 B1 | 11/2002 | Boppart et al. | |
| 6,524,249 B2 | 2/2003 | Moehring et al. | |
| 6,547,736 B1 | 4/2003 | Moehring et al. | |
| 6,575,922 B1 | 6/2003 | Fernside et al. | |
| 6,813,333 B2 * | 11/2004 | Karau et al. | 378/4 |
| 7,203,353 B2 | 4/2007 | Klotz et al. | |
| 2002/0016624 A1 | 2/2002 | Patterson et al. | |
| 2002/0077549 A1 | 6/2002 | Davidson et al. | |
| 2002/0091320 A1 | 7/2002 | Crutchfield et al. | |
| 2002/0095171 A1 * | 7/2002 | Belef | 606/200 |
| 2002/0099291 A1 | 7/2002 | Davidson et al. | |
| 2002/0114503 A1 * | 8/2002 | Klotz et al. | 382/131 |
| 2003/0199767 A1 | 10/2003 | Cespedes et al. | |
| 2003/0199768 A1 | 10/2003 | Cespedes et al. | |
| 2003/0204248 A1 | 10/2003 | Murphy | |
| 2004/0153138 A1 | 8/2004 | Murphy | |
| 2005/0033334 A1 * | 2/2005 | Santra et al. | 606/159 |
| 2007/0189443 A1 * | 8/2007 | Walter et al. | 378/4 |
| 2008/0004647 A1 | 1/2008 | To et al. | |
| 2008/0092623 A1 | 4/2008 | Lynch et al. | |
| 2008/0114235 A1 | 5/2008 | Unal et al. | |

\* cited by examiner

*Primary Examiner* — Tse Chen
*Assistant Examiner* — Joel F Brutus
(74) *Attorney, Agent, or Firm* — Seager, Tufte & Wickhem, LLC

(57) ABSTRACT

Methods for determining the size, pathology, and volume of embolic debris captured in an embolic protection filtering device. The methods may include providing an embolic protection filtering device and scanning the filtering device with a computed tomography scanner. The methods may also include analyzing digital images produced during the scanning step.

30 Claims, 2 Drawing Sheets

METHOD FOR DETERMINING SIZE, PATHOLOGY, AND VOLUME OF EMBOLIC MATERIAL

This application claims the benefit of U.S. Provisional Application No. 60/805,827, entitled "METHOD FOR DETERMINING SIZE, PATHOLOGY, AND VOLUME OF EMBOLIC MATERIAL," filed Jun. 26, 2006, the entirety of which is herein incorporated by reference.

FIELD OF THE INVENTION

The present invention pertains to embolic protection filtering devices. More particularly, the present invention pertains to methods for determining the size, pathology, and volume of embolic debris captured in an embolic protection filtering device.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

A wide variety of filtering devices have been developed for medical use, for example, intravascular use. In addition, a number of methods have been developed for determining the size, pathology, and volume of embolic debris captured in an embolic protection filtering device. Of the known filtering devices and methods, each has certain advantages and disadvantages. There is an ongoing need to provide alternative filtering devices and methods.

BRIEF SUMMARY

This disclosure provides alternative methods for determining the size, pathology, and volume of embolic debris captured in an embolic protection filtering device. The methods may include providing an embolic protection filtering device and scanning the filtering device with a computed tomography scanner. The methods may also include analyzing digital images produced during the scanning step.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

Figure 1:
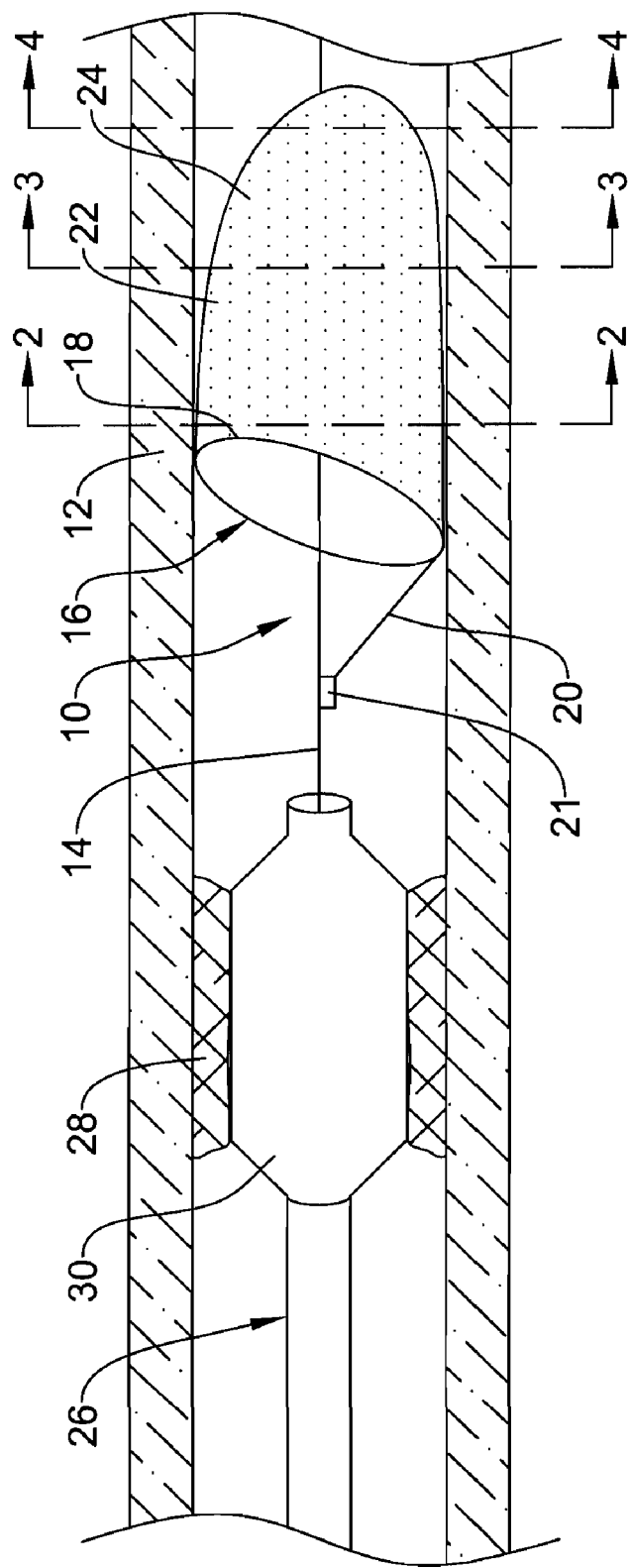
FIG. 1 is partial cross-sectional side view of an example filtering device disposed in a blood vessel.

The following description should be read with reference to the drawings wherein like reference numerals indicate like elements throughout the several views. The detailed description and drawings illustrate example embodiments of the claimed invention.

When a clinician performs an intravascular intervention such as angioplasty, atherectomy, and the like, embolic debris may dislodge from the blood vessel that can travel in the bloodstream to a position where it may impair blood flow, possibly leading to tissue damage. A number of other situations and/or interventions may also result in the mobilization of embolic debris. Accordingly, embolic protection filtering devices have been developed that can be disposed in the blood vessel downstream of the treatment site and expanded to capture debris.

FIG. 1 is a partial cross-sectional view of an example embolic protection filtering device 10 disposed within a blood vessel 12. Filtering device 10 can be delivered to a suitable target region, for example within blood vessel 12, using an appropriate delivery device (not shown) and removed after use with a suitable retrieval device (not shown). Device 10 may include an elongate shaft or filter wire 14 having an embolic protection filter 16 coupled thereto. Filter 16 includes a filter loop 18 and a filter membrane or fabric 22 coupled to filter loop 18. Filter membrane 22 can be drilled (for example, formed by known laser techniques) or otherwise manufactured to include a plurality of openings 24. These holes or openings 24 can be sized to allow blood flow therethrough but restrict flow of debris or emboli floating in the body lumen or cavity.

In general, filter 16 may be adapted to operate between a first generally collapsed configuration and a second generally expanded configuration for collecting debris in a body lumen. To this end, in at least some embodiments, loop 18 may be comprised of a "self-expanding" shape-memory material such as nickel-titanium alloy, which is capable of biasing filter 16 toward being in the second expanded configuration. Additionally, filter loop 18 may include a radiopaque material or include, for example, a radiopaque wire disposed about a portion thereof. Some further details regarding these and other suitable materials are provided below.

One or more struts 20 may extend between filter loop 18 and filter wire 14. Strut 20 may be coupled to filter wire 14 by a coupling 21. Coupling 21 may be one or more windings of strut 20 about filter wire 14 or may be a fitting disposed over an end of strut 20 to attach it to filter wire 14. The exact arrangement of struts 20 can vary considerably. One of ordinary skill in the art would be familiar with the various arrangements of struts 20 that are appropriate for a given intervention.

With filter 16 properly positioned in blood vessel 12, another medical device may be advanced over filter wire 14 in order to treat and/or diagnose a lesion 28. For example, a catheter 26 (such as the balloon catheter depicted in FIG. 1) may be advanced over filter wire 14 in order to expand lesion 28. Of course numerous other devices could just as easily be passed over filter wire 14 including any device designed to pass through an opening or body lumen. For example, the device may comprise any type of catheter (e.g., therapeutic, diagnostic, or guide catheter), a stent delivery catheter, an endoscopic device, a laproscopic device, variations and refinements thereof, and the like, or any other suitable device. Alternatively, another device may be advanced over or through its own guiding structure to a suitable location adjacent filter 16 in a manner that allows device 10 to perform its intended filtering function.

Filtering device 10 is generally designed to filter embolic debris that might be generated during the course of this medical intervention. For example, device 10 can be used to capture embolic debris that might be generated during the use of catheter 26 such as when a balloon 30 (coupled to catheter 26) is inflated. It should be noted, however, that device 10 may find utility in concert with essentially any procedure that has the potential to loosen and release embolic debris in to the blood stream or with the devices associated with such procedures.

Accurately determining the size, pathology, and volume of embolic debris captured in an embolic protection filtering device can be a challenging undertaking. Some methods for assessing the volume of material in a filter include visual inspection of a filter (removed from the body) and the assignment of a numeric (e.g., 0-4) grade that corresponds to visually "how full" the filter appears to be. This method is sufficient in some instances but it is highly subjective and provides no information on the size of debris particles or as to whether or not any particular pathology is associated with the particle. Other methods include emptying the debris captured by a filter and using a Beckman Coulter Counter to quantify the number of debris particles and approximate the size of the particles. Electron microscopy may also be used to assess particle size.

While the above methods serve a useful purpose in some interventions, other interventions may benefit from alternative methods. In at least some embodiments, the present invention provides alternative methods for determining the size, pathology, and volume of embolic debris captured in an embolic protection filtering device. For example, the methods for determining the size, pathology, and volume of debris captured in filtering device 10 might include a computed tomography scan of the filter and surrounding area. In doing so, several digital images are produced, which correspond to the individual scans or "slices" taken by the computed tomography scanner that can be analyzed. For example, the digital images can be analyzed to determine the size of the debris particles captured by filter 16, the volume of debris captured in filter 16 (which can be used to assess how "full" filter 16 is depending on the capacity of filter 16), and the pathology associated with the debris. With these pieces of data in hand, a clinician can adapt and/or conduct the filtering intervention that is best suited for the patient.

Turning now to some of the example methods contemplated, at least some include the step of providing a medical device such as an embolic protection filtering device. The filtering device may resemble assembly 10 and include filter wire 14 and filter 16 coupled to filter. Numerous other medical devices are also contemplated such as medical devices with a capturing capacity, catheters (e.g., therapeutic, diagnostic, or guide catheter), endoscopic devices, laproscopic devices, stents or stent-related devices, combinations thereof, and the like, or any other suitable device.

The method also may include the step of advancing the medical device through a body lumen to a position near an area of interest. For example, this might include advancing filter 16 through blood vessel 12 to a position adjacent lesion 28. Alternatively, the advancing step may include disposing a medical device in any other appropriate body lumen. The advancing step, particularly when filter 16 is used, may also include or be followed by the deployment of filter 16. Deployment can be understood as being the process and/or method for expanding filter 16 within vessel 12 to a configuration suitable for filtering debris. In embodiments where filter 16 includes a self-expanding filter loop 18, deployment may include removing constraints on filter 16 so that filter loop 18 can expand. With filter 16 deployed, it can now function by capturing the debris generated by an angioplasty, atherectomy, or other intervention that generates embolic debris.

At some point during the intervention, it may be desirable to scan filter 16 with a computed tomography scanner to produce a plurality of digital images. In some embodiments, this might include the removal of filter 16 from the body and the performance of a computed tomography scan outside the body. This might further include steps such as drying the filter and taking images with a suitable computed tomography scanner at every ⅙ of a degree turn or so.

In other embodiments, the computed tomography scan can be performed while filter 16 is still in the body lumen, again at every ⅙ of a degree turn or so. This later embodiment may be desirable for a number of reasons. For example, the scanning of filter 16 within the body allows for the clinician to monitor the size, pathology, and volume of the debris captured in filter 16 during the intervention and without the need for additional "non-treating" steps such as removal of filter 16. Moreover, because the size, pathology, and volume of the debris can be monitored in real time, it is possible for the clinician to tailor the intervention to the needs of a particular patient during the intervention and to provide a time-efficient treatment that best serves the needs of that patient.

It is worth noting that a "computed tomography" (or "CT") scan can be called different things by different individuals. In general, a computed tomography scan is a medical procedure that utilizes x-rays to generate a plurality of digital images (e.g., DICOM or Digital Imaging and Communications in Medicine images) of a target site from a number of different angles (e.g., at ⅙ of a degree turn or so all the way around the site to be imaged). Modern CT scanners boast impressive resolution and are a commonly used tool for skilled clinicians. Computed tomography is sometimes called computerized tomography, computer-aided tomography, or computed axial tomography (i.e., "CAT", CAT scanners, or CAT scans) and all of these names can be used interchangeably with computed tomography for the purposes of the present invention.

A number of different types of computed tomography scanners exist. For example, x-ray CT scanners, cone beam x-ray CT scanners, nano x-ray CT scanners, and the like, can be utilized for the scanning step. Although similar in function, these scanners may offer different performance considerations that may be appropriate for a given intervention. For example, these scanners can have different resolutions including resolutions where a single pixel of a digital image may correspond to about 0.1 micron in true dimensions. To put this resolution in perspective, such a resolution would cause a typical red blood cell to span approximately 300 pixels.

It should be noted that regardless of what exact type or model CT scanner is used, a computer is typically linked to the scanner for capturing and processing the digital images. The computer may be equipped with any number of different suitable software programs that assist the clinician in performing the intervention and/or studying the digital images. One such software program is 3D-DOCTOR®, which is available from Able software, Lexington, Mass.

With the appropriate CT scanner, the appropriate number of images (which, given that scans may be taken at every ⅙ of a degree turn, may be hundreds if not thousands), and the desired computer/software, the step of calculating the volume of the embolic material captured in the filter, assessing the size of captured embolic debris particles, and/or assessing the pathology of the debris can be carried out by analyzing the digital images.

When considering the calculating or analyzing step, it should first be noted that the digital images correspond to a number of "pixels". A pixel is the basic unit of the composition of a digital image or digital image display. Thus, a digital image is made up of a known number of pixels and each pixel gives a signal (which may be a particular color or grayscale) that contributes to the overall digital image that can be viewed on a suitable display. It can be appreciated that as the density of pixels (i.e., the number of pixels per unit length) increases, the "resolution" of the digital image increases. The resolution of a particular image is often described by the number of pixel per unit length. Higher resolutions generally correspond to better images. The use of the terms "pixel" and "resolution" are understood by those of ordinary skill in the art.

An individual digital image produced by the computed tomography scanner has a number of pixels that can correspond to a number of different structures that are being imaged. For example, an individual digital image may have pixels representing the body lumen or vessel 12 (i.e., when scanning is conducted within vessel 12), filter 16 or filter loop 18, free or unoccupied space within filter 16, and embolic debris disposed within filter 16 and/or captured on filter 16.

Figure 4:
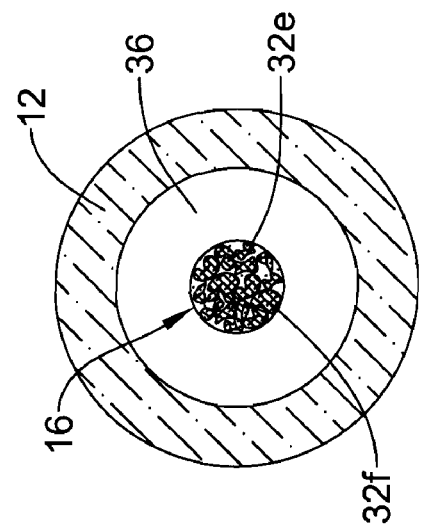
FIG. 4 is a cross-sectional view taken through line 4-4 of FIG. 1.
Figure 3:
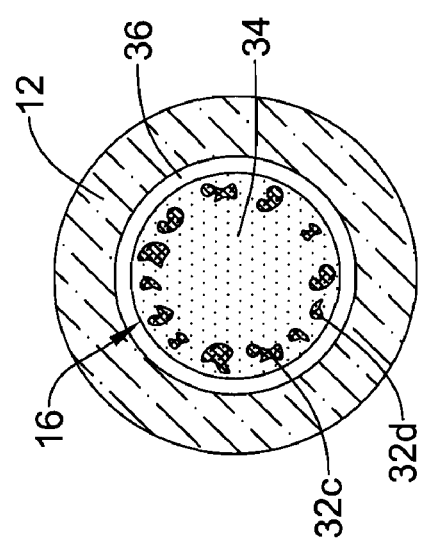
FIG. 3 is a cross-sectional view taken through line 3-3 of FIG. 1.
Figure 2:
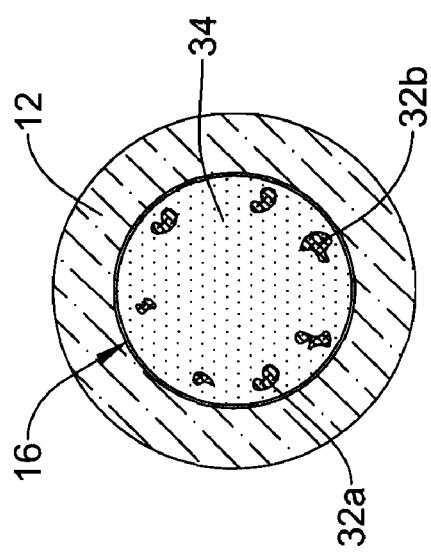
FIG. 2 is a cross-sectional view taken through line 2-2 of FIG. 1.

FIGS. 2-4 are highly diagrammatic representations of what might be seen on a digital image of filter 16. Each is meant to represent a digital image corresponding to a cross-sectional scan of filter 16. However, because these illustrations are highly diagrammatic, they are not meant to be exact duplicates of the output from an example CT scanner. In FIG. 2, which represents an image that is taken near filter loop 18, filter 16 can be seen as well as a number of particles of embolic debris (labeled as particles 32a/32b) and free or unoccupied space 34 within filter 16. Optionally, vessel 12 may also be seen depending on the locale of the scan. In some embodiments, particles 32a/32b are made up of a single pixel. In other embodiments, multiple or groups of pixels are occupied by a single particle 32a/32b. Because the amount of space in true dimensions that corresponds to an individual pixel is generally known beforehand, the size of particles 32a/32b can be assessed by counting the number of pixels occupying a particle. It can be seen that further along in the distal direction, more debris (e.g., particles 32c/32d) can be collected on filter 16 leaving a smaller amount of free space 34 as shown in FIG. 3. In addition, space 36 may also be seen between filter 16 and vessel 12. Finally, near the distal end of filter 16, a denser amount of debris (e.g., particles 32e/32f) can be seen collected on filter 16.

From the series of digital images collected during the scanning of filter 16, the desired calculations and/or analysis can be conducted. For example, the resolution of a particular image is typically known as well as the amount of space in true dimension corresponding to each pixel. From this known data, the area within filter 16 that is occupied by debris can be calculated, for example, by counting the number of pixels or groups of pixels that correspond to debris versus the number of pixels that correspond to unoccupied space 34 within filter 16. Once the area of the debris is known, the total volume of debris within filter 16 can be calculated, for example, by multiplying the debris areas by the amount of longitudinal length between individual scans or by averaging the debris areas across the total longitudinal length of filter 16 and multiplying by the length of filter 16. It can be appreciated that such calculations and/or analysis are typically carried out with the aide of a computer and computer software such as 3D-DOCTOR®.

Because the area within filter 16 is generally known or easily calculated, the "filtering capacity" of filter 16 can be determined. For example, the filtering capacity may be the total amount of space that potentially can be occupied by debris. If the volume of debris is monitored in real time, a clinician can track how full filter 16 is by comparing the volume of debris within filter 16 and comparing that volume with the filtering capacity of filter 16. When the volume of the embolic debris captured in filter 16 approaches the filtering capacity, filter 16 may be removed from the body and, if desired, replaced by another filter.

In addition, the pathology of an individual particle can also be assessed. For example, an individual particle can be assessed to determine if it includes or is a calcified plaque. Such an analysis may include the viewing of a digital image of a particular particle. Because computed tomography scanners use x-rays to image, the density of a particle can often be determined from the image. In general, particles that include or are calcified plaques have a higher density than other debris. Because the digital image of an individual particle may include pixels that use a gray or color scale to distinguish densities, potential or actual calcified plaques can be identified from the images. Depending on the particular diagnosis and treatment strategy of the clinician, further steps can be taken to break up the calcified plaque through any one of a number of known methodologies.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for quantifying embolic debris, comprising the steps of:
   advancing an embolic protection filtering device through a body lumen to a position near an area of interest, the device including an elongate shaft and a filter coupled to the shaft;
   capturing embolic material in the filter;
   scanning the body lumen with a computed tomography scanner to produce a plurality of digital images; and
   analyzing the digital images to calculate the volume of the embolic material captured in the filter.

2. The method of claim 1, wherein the step of scanning the body lumen with a computed tomography scanner to produce a plurality of digital images includes scanning the filter within the body lumen.

3. The method of claim 1, wherein the step of scanning the body lumen with a computed tomography scanner to produce a plurality of digital images includes scanning the filter with a cone beam x-ray computed tomography scanner.

4. The method of claim 3, wherein the digital images produced by the cone beam x-ray computed tomography scanner include a number of pixels.

5. The method of claim 4, wherein the pixels define a visual representation of the filter, space within the filter, or the embolic material disposed within the space.

6. The method of claim 5, further comprising the step of identifying groups of pixels that represent an individual particle of embolic material and determining the size of the individual particle.

7. The method of claim 6, further comprising the step of assessing the pathology of the individual particle.

8. The method of claim 7, wherein the step of assessing the pathology of the individual particle includes determining if the individual particle is a calcified plaque.

9. The method of claim 8, further comprising the step of breaking up the calcified plaque.

10. The method of claim 5, wherein the step of analyzing the digital images to calculate the volume of the embolic material captured in the filter includes using a computer to count the number of pixel representing embolic material on each individual digital image.

11. The method of claim 10, wherein each pixel correlates to a known volume and wherein the number of pixels counted on the digital images is multiplied by the known volume to calculate the volume of the embolic debris.

12. The method of claim 1, further comprising the step of removing the filter from the body lumen.

13. The method of claim 12, wherein the filter has a filtering capacity, and wherein the step of removing the filter from the body lumen occurs when the volume of the embolic debris captured in the filter approaches the filtering capacity.

14. A method for analyzing embolic debris captured in an embolic protection filtering device, comprising the steps of:
    advancing an embolic protection filtering device through a body lumen to a position near an area of interest, the device including an elongate shaft and a filter coupled to the shaft;
    capturing embolic material in the filter;
    scanning the body lumen with a cone beam x-ray computed tomography scanner to produce a series of digital images of the filter;
    wherein the digital images produced by the cone beam x-ray computed tomography scanner include a number of pixels that define a visual representation of the filter, a filtering space within the filter, or the embolic material disposed within the filtering space; and
    analyzing the pixels that define a visual representation of the embolic material disposed within the filtering space.

15. The method of claim 14, wherein the step of scanning the body lumen with a cone beam x-ray computed tomography scanner to produce a series of digital images of the filter includes scanning the filter within the body lumen.

16. The method of claim 14, further comprising the step of identifying groups of pixels that represent an individual particle of embolic material and determining the size of the individual particle.

17. The method of claim 16, further comprising the step of assessing the pathology of the individual particle.

18. The method of claim 17, wherein the step of assessing the pathology of the individual particle includes determining if the individual particle is a calcified plaque.

19. The method of claim 18, further comprising the step of breaking up the calcified plaque.

20. The method of claim 14, wherein the step analyzing the pixels that define a visual representation of the embolic material disposed within the filtering space includes counting the pixels that represent the embolic material disposed within the filtering space.

21. The method of claim 20, wherein counting the pixels that represent the embolic material disposed within the filtering space includes using a computer to count the number of pixel representing embolic material on each individual digital image.

22. The method of claim 21, wherein each pixel correlates to a known volume and wherein the number of pixels counted on the digital images is multiplied by the known volume to calculate the volume of the embolic debris captured in the filter.

23. The method of claim 14, further comprising the step of removing the filter from the body lumen.

24. The method of claim 23, wherein the filter has a filtering capacity, and wherein the step of removing the filter from the body lumen occurs when the volume of the embolic debris captured in the filter approaches the filtering capacity.

25. A method for filtering embolic debris, comprising the steps of:
    advancing an embolic protection filtering device through a body lumen to a position near an area of interest, the device including an elongate shaft and a filter coupled to the shaft, the filter having a filtering volume capacity;
    capturing embolic material in the filter;
    scanning the body lumen with a cone beam x-ray computed tomography scanner to produce a series of digital images of the filter;
    wherein the step of scanning the body lumen occurs with the filter in the body lumen;
    wherein the digital images produced by the cone beam x-ray computed tomography scanner include a number of pixels that define a visual representation of the filter, a filtering space within the filter, or the embolic material disposed within the filtering space;
    wherein each pixel represents a known volume;
    calculating the volume of embolic debris captured in the filter by counting the pixels that define a visual representation of the embolic material disposed within the filtering space and multiplying the number of pixels that define a visual representation of the embolic material disposed within the filtering space with the known volume; and
    removing the filter from the body lumen when the volume of the embolic debris calculated in the calculating step approaches the filtering volume capacity.

26. The method of claim 25, further comprising the step of identifying groups of pixels that represent an individual particle of embolic material and determining the size of the individual particle.

27. The method of claim 26, further comprising the step of determining if the individual particle is a calcified plaque.

28. The method of claim 27, further comprising the step of breaking up the calcified plaque.

29. A method for analyzing embolic debris captured in a medical device, comprising the steps of:
    advancing a medical device through a body lumen to a position near an area of interest;
    capturing embolic material with the medical device;
    scanning the body lumen with a cone beam x-ray computed tomography scanner to produce a series of digital images of the medical device;

wherein the digital images produced by the cone beam x-ray computed tomography scanner include a number of pixels that define a visual representation of the medical device, a space within the medical device, or the embolic material disposed within the space; and analyzing the pixels that define a visual representation of the embolic material disposed within the space.

30. A method for capturing embolic debris, comprising the steps of advancing a medical device having a capturing capacity through a body lumen to a position near an area of interest;

capturing embolic material with the medical device;

scanning the body lumen with a cone beam x-ray computed tomography scanner to produce a series of digital images of the medical device;

wherein the step of scanning the body lumen occurs with the medical device in the body lumen;

wherein the digital images produced by the cone beam x-ray computed tomography scanner include a number of pixels that define a visual representation of the medical device, a space within the medical device, or the embolic material disposed within the space;

wherein each pixel represents a known volume;

calculating the volume of embolic debris captured in the medical device by counting the pixels that define a visual representation of the embolic material disposed within the space and multiplying the number of pixels that define a visual representation of the embolic material disposed within the space with the known volume; and removing the medical device from the body lumen when the volume of the embolic debris calculated in the calculating step approaches the capturing capacity.

* * * * *